United States Patent
Zamfes

(10) Patent No.: US 6,276,190 B1
(45) Date of Patent: Aug. 21, 2001

(54) DIFFERENTIAL TOTAL-GAS DETERMINATION WHILE DRILLING

(76) Inventor: Konstandinos S. Zamfes, 1830-10th Ave. SW., Calgary, AB (CA), T3C 0J8

( * ) Notice: Subject to any disclaimer, the term of this patent is extended or adjusted under 35 U.S.C. 154(b) by 0 days.

(21) Appl. No.: 09/301,726

(22) Filed: Apr. 29, 1999

(30) Foreign Application Priority Data

Apr. 30, 1998 (CA) .................................................. 2236615

(51) Int. Cl.[7] .............................. E21B 47/00; E21B 49/08
(52) U.S. Cl. .................. 73/19.01; 73/19.09; 73/152.04; 73/152.42
(58) Field of Search ................. 73/19.01, 19.09, 73/152.04, 152.42

(56) References Cited

U.S. PATENT DOCUMENTS

| | | | |
|---|---|---|---|
| 2,328,555 | * 9/1943 | Hoover, Jr. ........................ | 73/152.04 |
| 3,196,664 | 7/1965 | Teal . | |
| 3,386,286 | * 6/1968 | Moore ............................... | 73/152.04 |
| 3,422,674 | * 1/1969 | Schroeter ........................... | 73/152.04 |
| 3,462,761 | * 8/1969 | Horeth et al. ................ | 73/152.04 X |
| 3,899,926 | 8/1975 | Haden . | |
| 4,174,629 | 11/1979 | Striegler ........................... | 73/152.42 |
| 4,319,482 | * 3/1982 | Bunner ............................. | 73/152.04 |
| 4,635,735 | 1/1987 | Crownover ........................ | 73/152.04 |
| 4,739,655 | 4/1988 | Greer et al. . | |
| 4,765,182 | 8/1988 | Boone . | |
| 4,833,915 | 5/1989 | Radd et al. . | |
| 4,887,464 | * 12/1989 | Tannenbaum et al. .......... | 73/152.04 |
| 5,467,823 | 11/1995 | Babour et al. . | |
| 5,469,917 | 11/1995 | Wolcott . | |

OTHER PUBLICATIONS

BetaTHERM NTC Thermistor Products Catalog 1994—95, pp. 8–10.

* cited by examiner

Primary Examiner—Daniel S. Larkin
(74) Attorney, Agent, or Firm—Sean W. Goodwin

(57) ABSTRACT

Apparatus and process is provided for establishing values of the quality of gaseous hydrocarbons in gas extracted from mud while drilling. Two rare earth sensors, without a coating, are exposed to the extracted gas. The first sensor is pre-calibrated and outputs a signal proportional to the relative concentration of light hydrocarbons. The second sensor is precalibrated and outputs a signal proportional to the relative concentration of heavy hydrocarbons. Preferably a second sensor is selected which, during calibration outputs a signal which is also proportional to the relative concentration of light hydrocarbons in a light sample gas and outputs a signal which is inversely proportional to the relative concentration of heavy hydrocarbons in a heavy sample gas. The difference of the two signals is obtained and is compared to the first sensor signal as being indicative of the quality of any hydrocarbons present in the extracted gases.

21 Claims, 6 Drawing Sheets

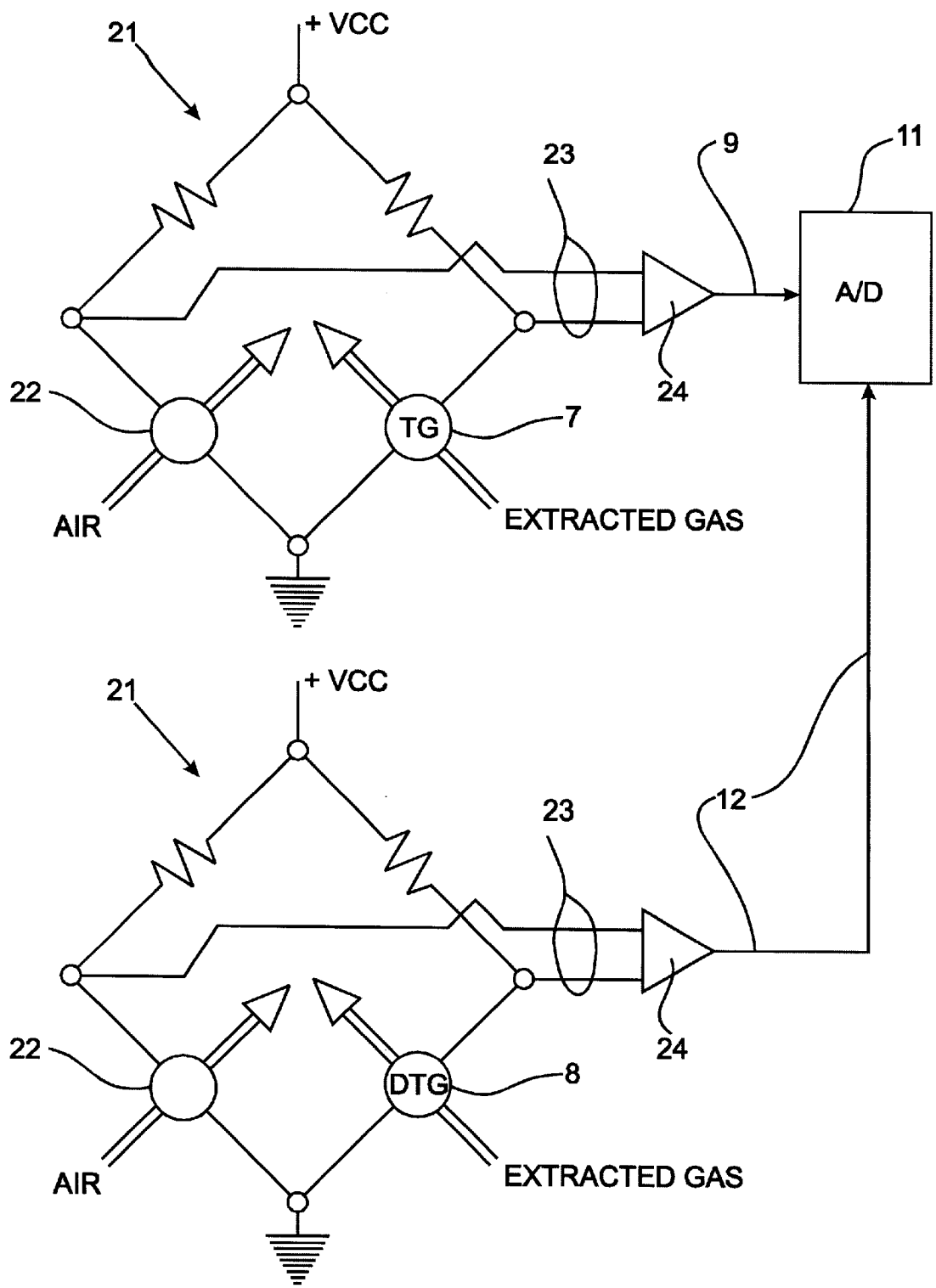

DIFFERENTIAL TOTAL-GAS DETERMINATION WHILE DRILLING

FIELD OF THE INVENTION

The invention relates to gas detection of hydrocarbons extracted from mud while drilling. In particular, two or more rare-earth sensors are used simultaneously as gas sensors.

BACKGROUND OF THE INVENTION

During the drilling of a well, mud is circulated downhole to carry away drill cuttings. Should gas be encountered, it becomes incorporated with the mud and is conveyed to the surface. In an active mud system, the mud is circulated in a loop; pumped from the mud tank, downhole to the bit, up to the surface, and back to the mud tank.

As the mud flows to the mud tank, an agitator, placed in the mud stream, causes contained gas to be liberated from the mud.

The liberated gas is directed past a gas sensor. One type of gas sensor is gas chromatography which produces a record of the constituents of the gas. Unfortunately, chromatography apparatus and methods of using same obtains only discrete analyses of gas in batches. A gas sample is occasionally selected and tested by the chromatograph. By the time the chromatograph is ready for the next sample, the drilling may have travelled a further ten feet or so and passed through and beyond a formation of interest. When the subsequent sample is obtained, the formation may then be uninteresting.

For producing a continuous gas trace, it is generally known to use a catalytic, rare earth or hot wire gas sensor. The sensor detects the presence of combustible gases. These devices are also called explosimeters and indicate the relative fraction of volatile hydrocarbons in a gas steam. Often these apparatus are used to determine if a gas mixture may be explosive.

The conventional gas sensor is a rare earth (hot-wire) sensor. An electrical current is passed though the sensor. The sensor heats up and dissipates energy dependent upon its ability to exchange energy with the surrounding environment. In these applications it is the gas flow and gas composition which affects the heat dissipation. Heat or power dissipation results in a change in the resistance of the sensor.

The sensor is epoxy coated for limiting the sensor from thermal effects and for excluding chemical interaction with the sensor's rare-earth portion.

The sensor output is recorded as a trace on a strip chart recorder or digitally on a computer and output for viewing on a screen. The presence of combustible gas shows up as an analog voltage output.

The difficulty with the prior art predominately lies in the interpretation of the continuous gas sensor output. This output responds to a high concentration of a predominantly methane gas with an output similar to a lesser amount of a heavier hydrocarbon.

There is therefore a demonstrated need for a real-time system which is capable of distinguishing heavier hydrocarbons (indicative of oil) from lighter hydrocarbons (representing coal gas or methane) while drilling, thereby affording the drilling operator an onsite ability to assess the value of the well.

SUMMARY OF THE INVENTION

The present invention is based upon a discovery that rare earth sensors are more usefully applied to gas detection, and more generally, fluid identification, if stripped of their epoxy coating. Without the epoxy coating, the rare earth oxides of the sensor are subject to absorption and electrochemical interactions with the measured fluid, in addition to the thermal effects. Stripped of their coatings, individual sensors have individual responses. By carefully selecting certain sensors which respond differently and predictably to known ranges of hydrocarbons, more useful analyses of the relative concentrations within gases can be made.

According to one embodiment of the present invention, two rare earth sensors are provided. Each sensor is sensitive to different ranges of hydrocarbons in sampled gases. Changes in relative concentration of the selected hydrocarbon in the sampled gas results in a change in the output of the corresponding sensor. Thus, where the sampled gas is a mixture of light and heavy hydrocarbon gases, the two sensors generally respond differently as the relative concentrations in the mixture change. The different response can be accentuated by obtaining the difference of the two signals. So, as drilling progresses through subterranean zones having different qualities of gases, the gas sensors provide distinctive output dependent upon whether they detect light or heavy hydrocarbons. For the first time, these different gas qualities are distinguishable, whereas previously, one only knew that volatile hydrocarbons merely existed in determinable relative concentrations.

Accordingly, in a broad aspect, a novel process is provided for distinguishing the quality of hydrocarbons extracted from gas encountered while drilling, comprising the steps of:

providing a first rare-earth metal oxide gas sensor which is sensitive to the concentration of a first group of components in a hydrocarbon mixture;

providing a second rare-earth metal oxide gas sensor which is sensitive to the concentration of a second group of components;

exposing the metal oxide of the first sensor to the extracted gas and outputting a first signal indicative of the concentration of the first group of components in the gas, preferably proportional to the relative concentration of light hydrocarbons;

exposing the metal oxide of the second sensor to the extracted gas and outputting a second signal indicative of the concentration of the second group of components in the gas, preferably inversely proportional to the relative concentration of heavy hydrocarbons; and obtaining the difference between the first and second signals for establishing a differential third signal which is demonstrative of the quality of the gas extracted from the well.

Preferably, the first sensor is sensitive to light hydrocarbons (like methane), but characteristically also responds to any hydrocarbons (total-gas) in the gas sample. The second sensor is sensitive to heavier hydrocarbons (such as ethane through pentane). Further, the first sensor preferably produces an increasing signal at increasing light hydrocarbon content and the second sensor produces a decreasing signal with increasing heavier hydrocarbon content. Accordingly, the difference in quality becomes even more marked as the hydrocarbon content increases. The resultant difference accentuates the quality characteristics of the gas sample rather than speaking merely of quantity or concentration.

The apparatus and methods disclosed in the present invention now enables a log analyst to easily visualise, detect and distinguish the distinct nature of a downhole gas event, whether it be the crossing and detection of a coal seam producing light gas, or the crossing of an interface of gas (light hydrocarbons), oil (heavier hydrocarbons), or water (no hydrocarbons).

BRIEF DESCRIPTION OF THE DRAWINGS

FIG. 4 is a typical circuit for conditioning the signal from the gas sensors;

DETAILED DESCRIPTION OF THE PREFERRED EMBODIMENT

Figure 1:
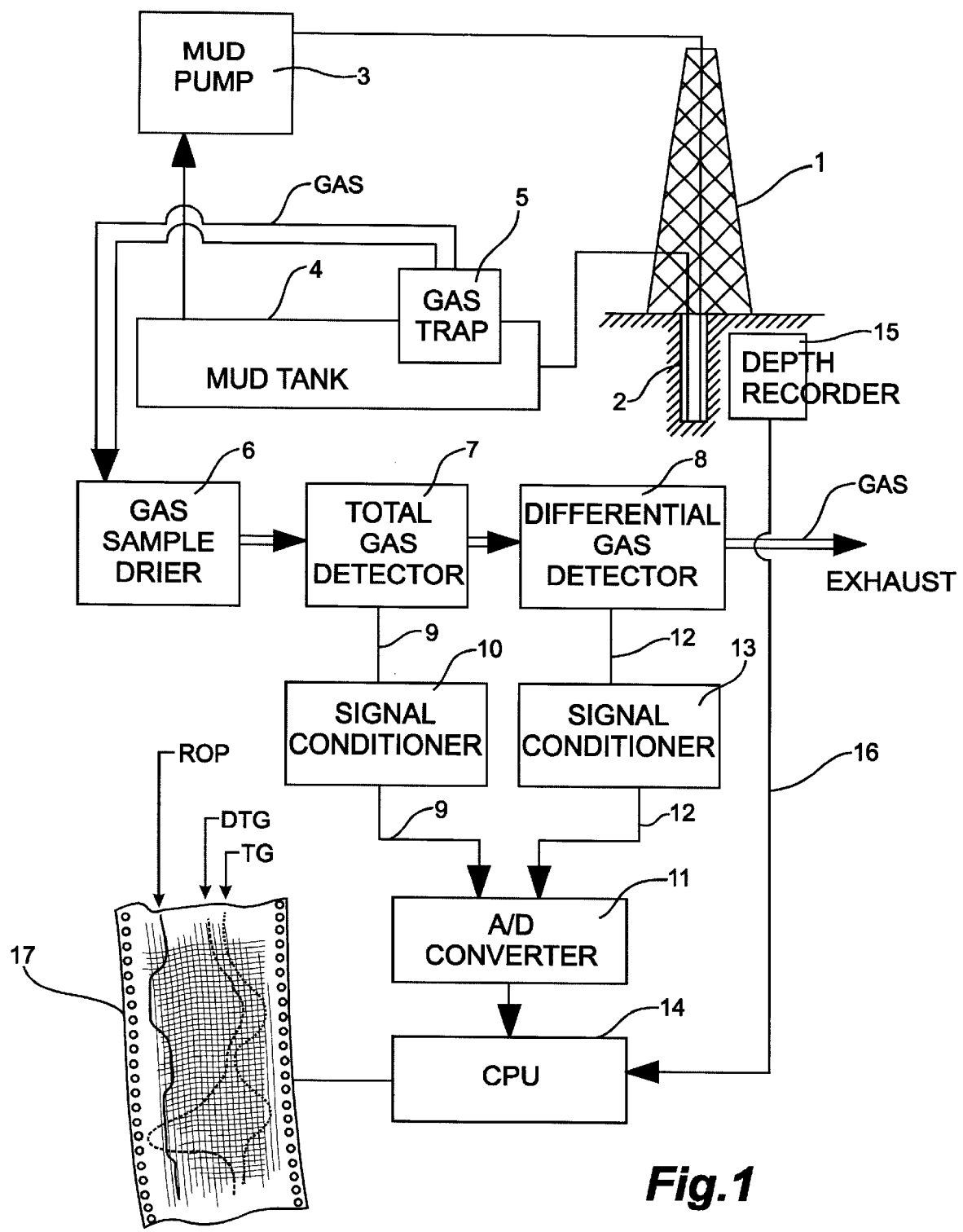
FIG. 1 is a: flow chart of the mud flow system, the gas sampling, the gas detection, and the sensor signal output on a strip chart.

Having reference to FIG. 1, a drilling rig 1 drills a well 2 into a formation. Mud M is used to aid in drilling and conveying cuttings from the well 2 to the surface. Mud M is delivered in a closed loop system comprising a mud pump 3 which circulates mud M to the well 2, out of the well, to a mud tank 4 for separating solids from returning mud M, and back to the mud pump 3. A gas trap 5 separates or extracts gas (GAS) from the mud M. The extracted gas passes through sample drier 6 to produce a dry gas sample.

The gas sample GAS is directed through a first gas sensor 7 and through second gas sensor 8. The gas sample GAS is then exhausted to atmosphere (subject to environmental constraints, e.g. if the gas is not sour).

The first gas sensor 7 is a total-gas (TG) sensor and is sensitive to variable relative concentrations of predominately methane ($CH_4$) in the gas sample. The TG sensor responds to all hydrocarbons regardless of the weight of the hydrocarbon, producing an output signal as if the sampled gas was equivalent to methane.

The second gas sensor 8 is sensitive to variable relative concentrations of heavier hydrocarbons such as ethane ($C_2H_6$) through pentane ($C_5H_{12}$) in the dried gas GAS. Preferably, when exposed to light hydrocarbons, the second sensor 8 behaves similarly to the first sensor, however, when exposed to heavy hydrocarbons, it behaves in an opposite manner as described in greater detail below.

The first and second sensors 7,8 are electrically positioned in a Wheatstone bridge 21 (FIG. 4) for applying a voltage across the sensor. Sufficient voltage is applied to heat the sensor. When gases are conducted through the sensors which they are sensitive to, the sensor's resistivity changes and the current flow through the sensor changes. The output from the Wheatstone bridge is a variable voltage output.

The first sensor 7 produces a variable voltage signal 9 which passes through a signal conditioner 10 and is routed to an analog-to-digital A/D converter 11. The second sensor 8 produces a signal 12 which passes through a signal conditioner 13 and is also routed to the A/D converter 11. A multiplexer or the like (not shown) can be used to handle multiple sensor signals 9, 12 with one A/D converter 11. Digital output from the A/D converter 11 is routed to a CPU 14. An electronic depth recorder 15 produces a digital recorder signal 16 which is also routed to the CPU 14.

The CPU 14 processes the sensor signals 9 and 12 and obtains their difference. Specifically, sensor signal 12 is subtracted from sensor signal 9 to produce a value representing a differential total-gas (DTG) signal. The depth recorder signal 16 is processed to calculate the rate of penetration (ROP) during drilling.

Additional information is processed by the CPU as necessary to calculate other parameters including mud fluid lag. Gas sensor output cannot be directly related to the actual position of the drilling bit due to the lag associated with the return of the mud from the bit to the gas trap and thus to the gas sensor. This information is plotted in a graphical format - depicted in the form of a chart 17 or on a computer screen.

The sensors 7,8 are comprised of a rare-earth, transition metal oxide sensors which are sintered and sandwiched between metallized surfaces or electrodes. It is known that the resistivity of the metal oxide to temperature is non-linear which makes the sensor ideal for temperature sensing applications. In this implementation, if current is applied, then the sensor is self-heating. If heat is constantly dissipated then the resistivity remains constant and the voltage across the metal oxide will be constant. Alternatively, if the surrounding environment causes the heat dissipation to vary (as it will if the quality or concentration of hydrocarbon changes) then the current or the voltage will vary.

Figure 2:
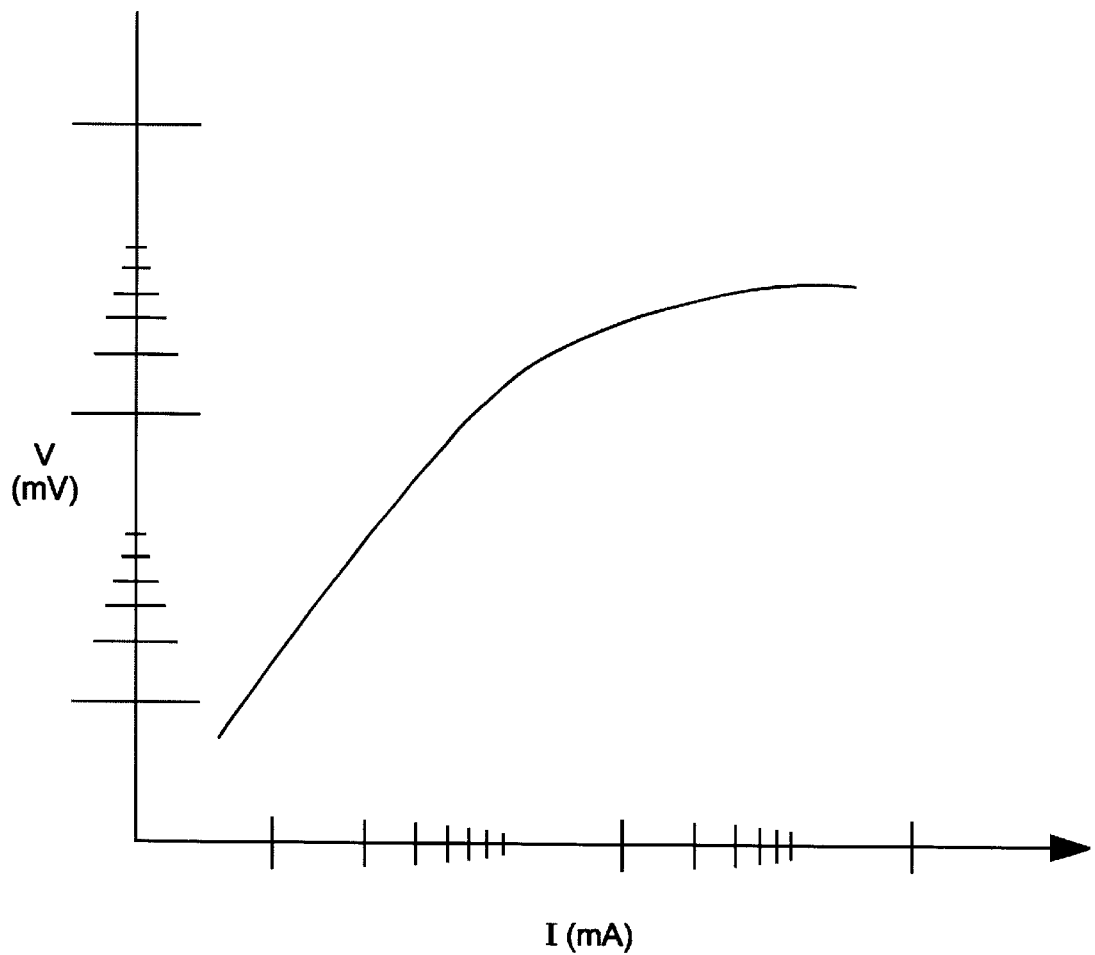
FIG. 2 is a typical graph of voltage versus amperage for a thermistor sensor in a static fluid environment.

Having reference to FIG. 2, the typical response of an epoxy-coated, bead-type rare-earth sensor is shown as applied in a static fluid environment. Such a sensor is exemplified by a rare-earth thermistor as supplied by BetaTHERM Corporation, Shrewsbury, Mass. As the voltage is varied, the resistivity changes and the current changes accordingly to match the heat dissipation.

Also, for the purposes of the present invention, these rare earth sensors are used for both the first and second sensors 7,8. Sufficient variability exists between each commercially available thermistor sensor to enable selection of two having different responses when exposed to different gases.

Figure 3A:
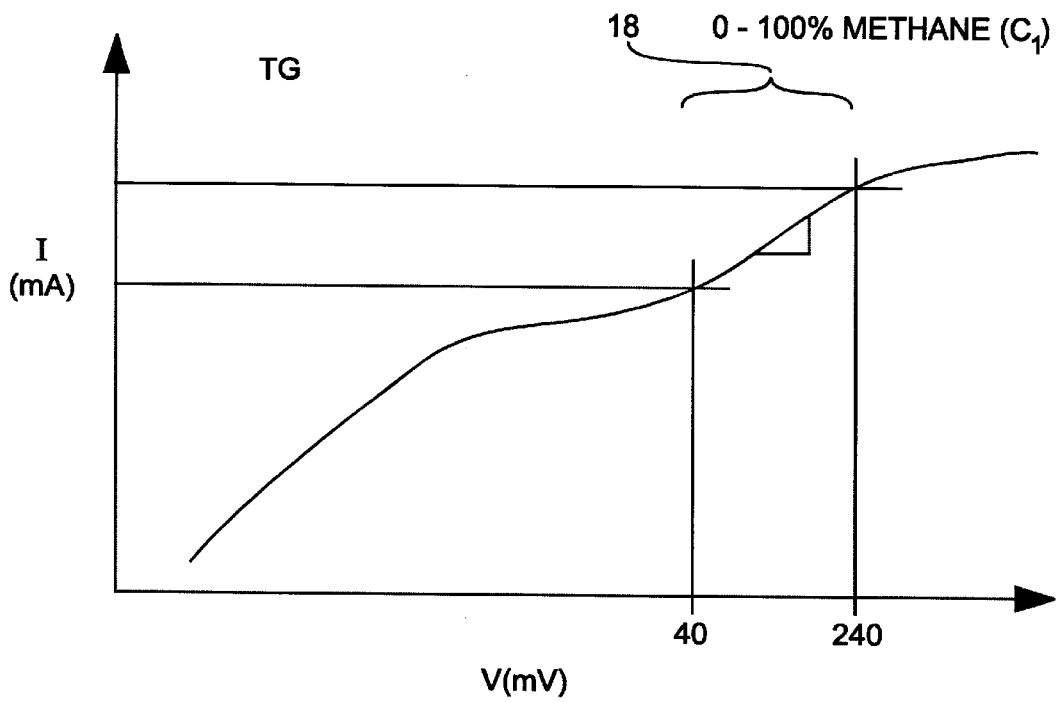
FIG. 3a is a graph depicting the current and voltage response of a total-gas sensor for detecting light hydrocarbons.
Figure 3B:
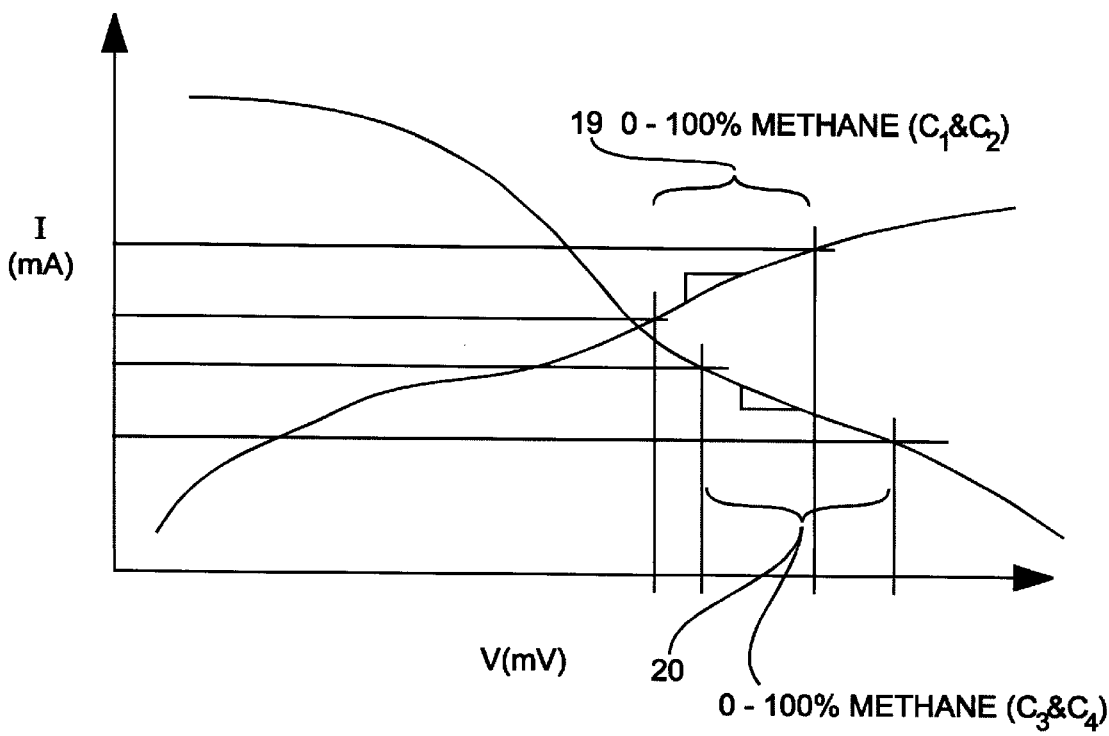
FIG. 3b is a graph depicting the current and voltage response of a differential total-gas sensor for detecting heavier hydrocarbons.

Turning then to FIGS. 3a and 3b, current-voltage curves are illustrated for the first and second sensors 7,8 respectively.

For both the TG and DTG sensors 7,8 a commercial thermistor sensor is first stripped of its epoxy to expose the metal oxide. The sensor is powered to about 40–200 mV so that it self-heats; the temperature of the sensor approaching about 300° C. The sensors resistivity varies with temperature. Various concentrations of a known hydrocarbon gas are passed across the sensor, the sensor dissipates heat, the resistivity changes and the resulting change in current is observed. Currents of about 100 mA are typical.

Having reference to FIG. 3a, a range of 0 to 100% concentration of methane is passed across an exposed metal oxide sensor for selection and calibration of the first gas sensor 7. The response of a successful first gas sensor 7 demonstrates a substantially consistent increase 18 in current for increasing concentrations of methane.

In a similar test used for the TG sensor 7, and having reference to FIG. 3b, this time two different gas mixtures are passed across another exposed metal oxide sensor for selection and calibration of the second gas sensor 8. For mixtures containing only methane and ethane (one can use natural gas also), the selected gas sensor 8 demonstrates a substantially consistent increase 19 in current for increasing concentrations of the gas mixture. For propane and butane mixtures (being heavier hydrocarbons) the same selected sensor 8 demonstrates a substantially consistent decrease 20 in current for increasing concentrations of the gas mixture. For a similar range of voltage input, it is desirable to select a second sensor 8 which demonstrates the greatest divergence between the increasing current and decreasing current responses 19,20. Accordingly the second gas sensor responds in two ways on two different mixtures of gas.

FIG. 4 illustrates the signal conditioning circuit 10,13 for each sensor 7,8 based on Wheatstone bridges 21 for accepting the sensor output current and outputting an electric signal 9,12 proportional to concentration of the gases sensed by the first or second sensors 7,8. A bridge power VCC is operated in the range of 2.5–5 volts. A balancing sensor 22 is operated on air. The balancing sensor is an unaltered commercial variety of the sensors used for the first and second sensors 7,8. The bridge output 23 passes through an amplifier 24 before directing the sensor millivolt output signals 9, 12, respectively to the A/D converter 11.

Figure 5:
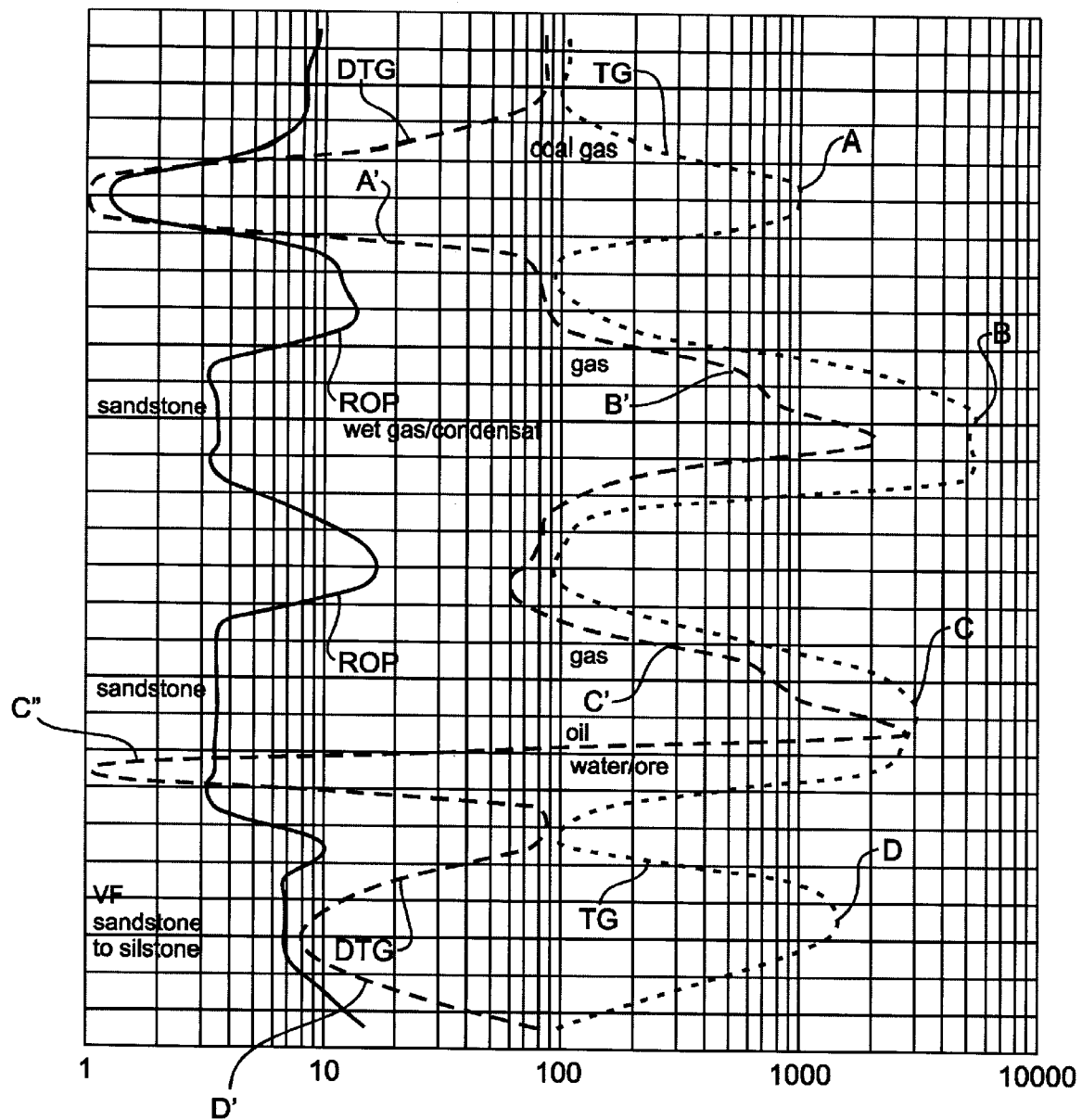
FIG. 5 is a chart trace of the output of the total-gas and differential total-gas sensors, the differential between the sensor signals and the rate of production for drilling through a sandstone formation according to the first example.

When exposed to a mixture of gases, generally both sensors 7,8 respond with increasing current output 9,12 for the lighter hydrocarbons with a subtraction operation reducing magnitude of the positive value of the resulting DTG output. For gases having high concentration of light hydrocarbons, signal 9 less signal 12 can result in a DTG signal pass through zero or even becoming negative. An example is shown in FIG. 5 as negative peak A'.

However, as a gas mixture becomes heavier, the DTG sensor 8 causes the current output 12 to drop significantly, with the subtraction operation resulting in an increased net DTG output. An example is shown in FIG. 5 as positive peak B'.

The numerical ratio of the values of the TG signal and the DTG signal can also be used as a simple means for establishing the relative concentration of heavy or light hydrocarbons in the extracted gas.

EXAMPLES

Figure 6:
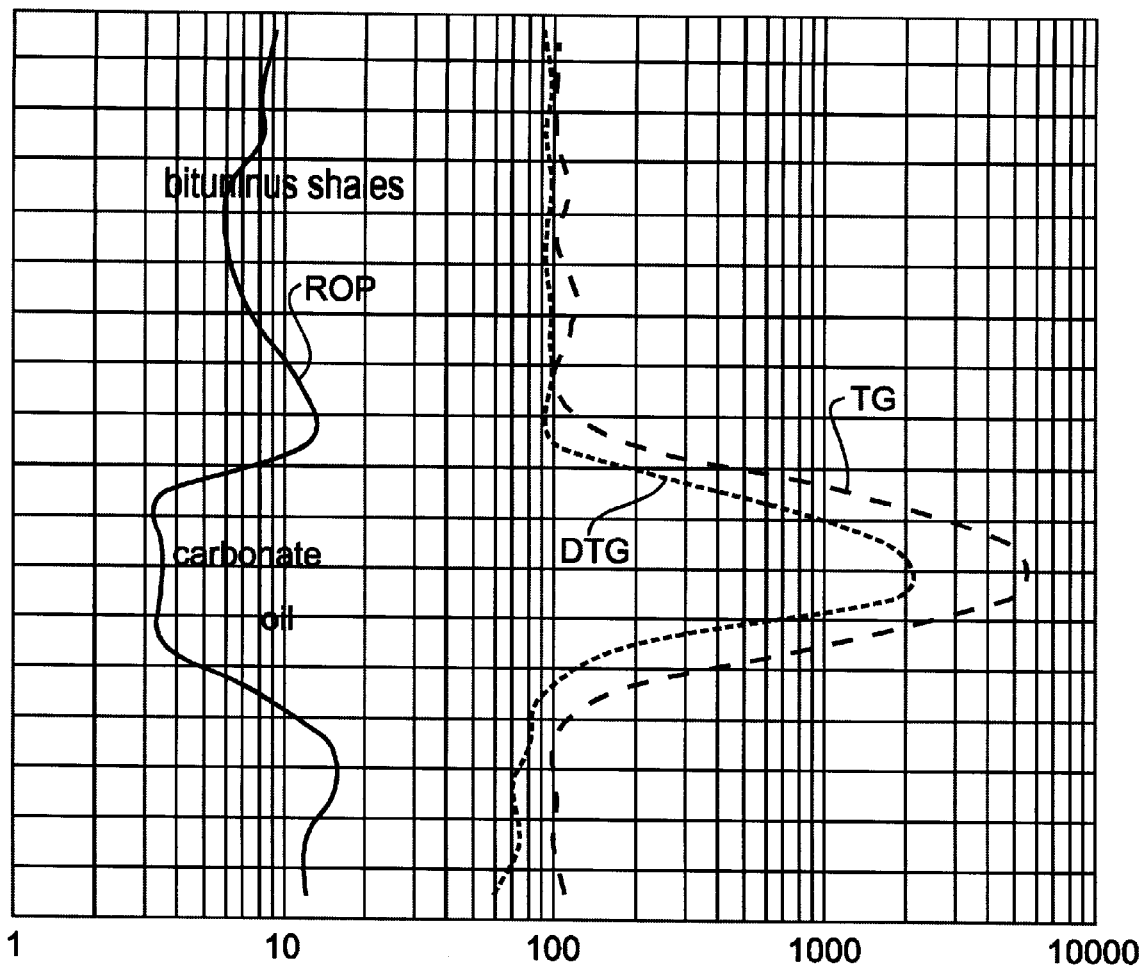
FIG. 6 is a chart trace for drilling through bitumous shales and carbonates, according to the second example.

As an example, in operation on actual wells drilled in Alberta, CANADA, and referring to FIGS. 5 and 6, gas was extracted from mud while drilling and was passed through first and second sensors 7,8 selected and operated according to one embodiment of the present invention.

In FIG. 5, the first sensor 7 outputs a signal 9 (TG) which is indicative of the concentration of hydrocarbons in the sampled gas GAS (measured as equivalent methane). This TG signal is shown on the strip chart 17, which also happens to be the conventional case in the prior art. In contradistinction with the prior art, the second gas sensor 8 outputs a signal 12 which is indicative of the concentration of heavier hydrocarbons. The signals 9,12 are combined by subtraction to form a differential value (DTG) which is shown on the chart 17. Only the differential value DTG is shown and not the raw signal 12.

Note that, while the TG signal demonstrates four clear deviations from the background baseline as positive peaks A,B,C, and D, the DTG signal correspondingly demonstrates a negative peak A', two positive peaks B', C', and a last negative peak D'.

While the prior art may interpret each of the four peaks A,B,C, and D as being indicative only of the presence of hydrocarbons, the prior art is unable to distinguish the specific nature of hydrocarbon's quality. Using the DTG signal in combination with the TG signal—namely peaks A',B',C'and D', quality is determinable.

For the first TG peak A, the deep negative DTG peak A' illustrates the predominance of light hydrocarbons which, in this case, turned out to be coal gas.

In the case of the second TG peak B, both the TG curve B and the DTG curve B' were positive indicating a heavier hydrocarbon component which turned out to be wet gas and condensate (oil).

For the third TG peak C, both TG and DTG curves C,C' were again positive indicating a heavier hydrocarbon component which turned out to be oil. A sudden negative component C" represents an oil/water interface.

Lastly, for the fourth TG peak D, the negative DTG peak D' illustrated the presence once again of a lighter hydrocarbon which turned out to be gas in a sandstone to siltstone transition.

Turning to the second example well shown in FIG. 6, representing a well drilled in bituminous shales, note that both the TG and DTG curves became positive through a zone of carbonate oil, properly indicating not only the presence of hydrocarbons (prior art) but has been enhanced to demonstrate the presence of the heavier bituminous hydrocarbon components.

The embodiments of the invention in which an exclusive property or privilege is claimed are defined as follows:

1. A process is provided for establishing values indicative of the quality of gaseous hydrocarbons in gas extracted from drilling mud, comprising the steps of:
   selecting a first metal oxide gas sensor which is sensitive to the concentration of a first group of hydrocarbons;
   selecting a second metal oxide gas sensor which is sensitive to the concentration of a second group of hydrocarbons;
   exposing the metal oxide of the first sensor to the gas so that the first sensor outputs a first signal proportional to the relative concentration of the first group of components in the extracted gas;
   exposing the metal oxide of the second sensor to gas so that the second sensor outputs a second signal proportional to the relative concentration of the second group of components in the extracted gas; and
   obtaining the difference between the first and second signals to establish a differential value which is demonstrative of the quality of the extracted gas.

2. The process as recited in claim 1 wherein the first group of components in the extracted gas are predominantly methane.

3. The process as recited in claim 2 wherein the second group of components in the extracted gas are predominately heavier than methane.

4. The process as recited in claim 3 wherein the second group of components in the extracted gas are predominately ethane through pentane.

5. The process as recited in claim 1 wherein the sensitivity of the first metal oxide gas sensor demonstrates a decreased resistivity under applied voltage for increasing concentrations of methane.

6. The process as recited in claim 1 wherein the sensitivity of the second metal oxide gas sensor:
   (a) demonstrates a decreasing resistivity under an applied voltage for gases containing increasing concentrations of methane and ethane; and
   (b) demonstrates an increasing resistivity under an applied voltage for gases containing increasing concentrations of propane and heavier hydrocarbons.

7. The process as recited in claim 1 further comprising:
processing the first signal through a first bridge circuit; and
processing the second signal through a second bridge circuit.

8. The process as recited in claim 7 wherein the first and second bridge circuits each use a balancing metal oxide gas sensor exposed to air.

9. The process as recited in claim 1 wherein the first metal oxide gas sensor demonstrates an increasing output for increasing concentrations of methane.

10. The process as recited in claim 1 further comprising:
creating a plot of drilling information including rate of penetration as a function of time;
plotting the first signal on the plot as a function of time; and
plotting the differential value on the plot as a function of time.

11. The process as recited in claim 1 wherein the second metal oxide gas sensor:
demonstrates an increasing output for gases containing increasing concentrations of methane and ethane; and
demonstrates a decreasing output for gases containing increasing concentrations of propane and heavier.

12. Apparatus for establishing the quality of gaseous hydrocarbons in gas extracted from drilling mud, comprising:
a first metal oxide gas sensor which is sensitive to the concentration of a first group of hydrocarbons which, when exposed to the extracted gas, outputs a first signal indicative of the relative concentration of the first group of hydrocarbons in the extracted gas;
a second metal oxide gas sensor which is sensitive to the concentration of a second group of hydrocarbons which, when exposed to the extracted gas, outputs a second signal indicative of the relative concentration of the second group of hydrocarbons in the extracted gas; and
means for obtaining the difference between the first and second signals to produce a value demonstrative of the relative concentrations of the second group of hydrocarbons in the extracted gas.

13. Apparatus as recited in claim 12 wherein:
the first group of hydrocarbons are light hydrocarbons; and
the second group of hydrocarbons are heavy hydrocarbons.

14. Apparatus as recited in claim 13 wherein:
the first metal oxide gas sensor outputs a first signal which is proportional to the relative concentration of light hydrocarbons in the extracted gas; and
the second metal oxide gas sensor outputs a second signal, which when exposed to the first group of hydrocarbons, is proportional to relative concentrations of light hydrocarbons, and when exposed to the second group of hydrocarbons, is inversely proportional to relative concentrations of heavier hydrocarbons.

15. Apparatus as recited in claim 14 wherein the light hydrocarbons are methane and ethane and the heavier hydrocarbons are propane and heavier hydrocarbons.

16. Apparatus as recited in claim 12 wherein the means for obtaining the difference between the first and second signals comprises: a converter for converting the first and second signals from analog to digital; and a digital computer.

17. Apparatus for establishing the quality of gaseous hydrocarbons in gas extracted from drilling mud, comprising:
a first metal oxide gas sensor which is sensitive to the concentration of a first group of hydrocarbons which, when exposed to the extracted gas, outputs a first signal indicative of the relative concentration of the first group of hydrocarbons in the extracted gas;
a second metal oxide gas sensor which is sensitive to the concentration of a second group of hydrocarbons which, when exposed to the extracted gas, outputs a second signal indicative of the relative concentration of the second group of hydrocarbons in the extracted gas;
an analog to digital convertor which converts the first signal to a first output value and which converts the second signal to a second output value; and
a processor which obtains the difference between the first and second output values to produce a differential value demonstrative of the relative concentrations of the second group of hydrocarbons in the extracted gas.

18. Apparatus as recited in claim 17 wherein:
the first metal oxide gas sensor outputs a first signal which increases with increasing concentrations of hydrocarbons in the extracted gas; and
the second metal oxide gas sensor outputs a second signal, which increases with increasing concentrations of light hydrocarbons, and deceases with increasing concentrations of heavier hydrocarbons.

19. Apparatus as recited in claim 18 wherein the light hydrocarbons are substantially methane and the heavier hydrocarbons are substantially ethane and heavier hydrocarbons.

20. A process is provided for establishing values indicative of the quality of gaseous hydrocarbons in gas extracted from drilling mud, comprising the steps of:
selecting a first sensor which is sensitive to the concentration of a first group of hydrocarbons;
selecting a second sensor which is sensitive to the concentration of a second group of hydrocarbons;
exposing the first sensor to the gas so that the first sensor produces a first output value proportional to the concentration of the first group of components in the gas;
exposing the second sensor to gas so that the second sensor outputs a second output value proportional to the concentration of the second group of components in the gas; and
obtaining the difference between the first and second output values whereby the differential value is demonstrative of the quality of the gas.

21. The process as recited in claim 20 further comprising:
creating a plot of drilling information including rate of penetration as a function of time;
plotting the first output value on the plot as a function of time; and
plotting the differential value on the plot as a function of time.

* * * * *